Figure 1:
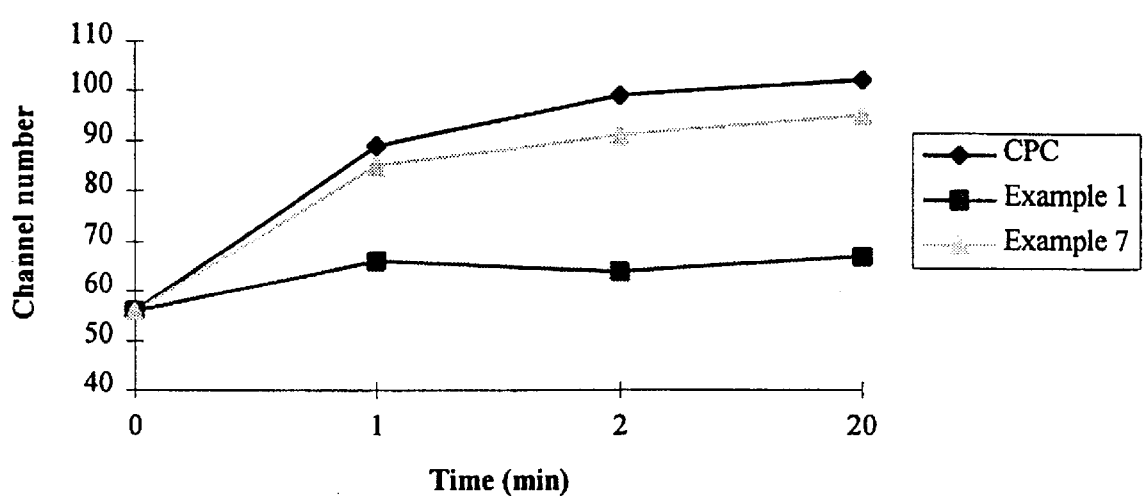

United States Patent [19]
Wicks et al.

[11] Patent Number: 6,117,417
[45] Date of Patent: Sep. 12, 2000

[54] MOUTHWASH COMPOSITION COMPRISING CETYLPYRIDINIUM CHLORIDE AND AN AMPHOTERIC SURFACTANT

[75] Inventors: Mark Andrew Wicks, Walton-on-Thames; Peter Scott McConville, Isleworth; Paula Walsh, surbiton, all of United Kingdom

[73] Assignee: SmithKline Beecham p.l.c., Brentford, United Kingdom

[21] Appl. No.: 09/194,531

[22] PCT Filed: May 20, 1997

[86] PCT No.: PCT/EP97/02714

§ 371 Date: Nov. 25, 1998

§ 102(e) Date: Nov. 25, 1998

[87] PCT Pub. No.: WO97/46217

PCT Pub. Date: Dec. 11, 1997

[30] Foreign Application Priority Data

May 31, 1996 [GB] United Kingdom .................... 9611364

[51] Int. Cl.⁷ ................. A61K 7/16; A61K 7/22
[52] U.S. Cl. .................................. 424/54; 424/49
[58] Field of Search ........................... 424/49–58

[56] References Cited

U.S. PATENT DOCUMENTS 4,693,888   9/1987   Miyahara et al. .................. 424/49

FOREIGN PATENT DOCUMENTS

| 0 408 174 | 1/1991 | European Pat. Off. . |
| 0 485 616 | 5/1992 | European Pat. Off. . |
| 24 42 712 | 3/1976 | Germany . |
| WO 90 15592 | 12/1990 | WIPO . |
| WO 95 31175 | 11/1995 | WIPO . |

OTHER PUBLICATIONS

Derwent Publication Ltd., London, GB; AN 91–092240, Jul. 5, 1989, see abstract & JP03038516A, published Jul. 5, 1989.

Derwent Publication Ltd., London, GB; AN 95–220935, May 23, 1995, see abstract & JP07133492A, published May 23, 1995.

*Primary Examiner*—Shep K. Rose
*Attorney, Agent, or Firm*—Nora Stein-Fernandez; Janice E. Williams; Charles M. Kinzig

[57] ABSTRACT

Mouthwash compositions are described comprising cetylpyridinium chloride and amidobetaine amphoteric surfactants of formula (I): $RC(O)NH(CH_2)_a N^+(R^1)(R^2)(CH_2)_b CO_2^-$, wherein R is $C_{10-20}$ alkyl; $R^1$ and $R^2$ are independently $C_{1-4}$ alkyl; a is an integer from 1 to 4; and b is an integer from 1 to 4.

7 Claims, 1 Drawing Sheet

100 μl of actives mean fluorescence channel

| Time | CPC | Ex. 1 | Ex. 7 |
|------|-----|-------|-------|
| 0    | 56  | 56    | 56    |
| 1    | 89  | 66    | 85    |
| 2    | 99  | 64    | 91    |
| 20   | 102 | 67    | 95    |

Effects of actives on membrane potential of S. mutans

MOUTHWASH COMPOSITION COMPRISING CETYLPYRIDINIUM CHLORIDE AND AN AMPHOTERIC SURFACTANT

This application is a 371 of PCT/EP97/02714 filed May 20, 1997.

The present invention relates to a mouthwash composition cetyl pyridinium chloride (CPC) and an amphoteric surfactant.

The use of cationic antibacterial agents such as CPC in oral hygiene compositions has been widely advocated as a means of reducing the bacterial plaque population and this may be beneficial in the prophylaxis and/or treatment of mouth odour, periodontal disease, plaque, calculus and/or caries.

Whilst mouthwashes comprising CPC are available these can suffer the disadvantage of reduced efficacy due to CPC deactivation caused by the presence of any anionic excipients within such mouthwashes.

Although nonionic surfactants have previously been suggested for use with cationic antibacterial agents it has now been found that many such surfactants can reduce the efficacy of mouthwashes comprising CPC.

Surprisingly it has now been found that particular amphoteric amidobetaine surfactants are more compatible with CPC than nonionic surfactants such as polyethoxylated sorbitol esters, polycondensates of ethylene oxide (polaxamers) and polyethoxylated hydrogenated castor oils.

The present invention therefore provides a mouthwash composition comprising a bacteriostatically effective amount of CPC; an orally acceptable carrier or excipient and an amidobetaine of the formula:

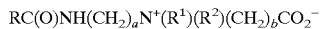

$$RC(O)NH(CH_2)_a N^+(R^1)(R^2)(CH_2)_b CO_2^-$$

wherein

R is $C_{10-20}$ alyl, preferably $C_{12-16}$ alkyl;

$R^1$ and $R^2$ are independently $C_{1-4}$ alkyl, preferably methyl;

a is an integer from 1 to 4, preferably 3; and b is an integer from 1 to 4, preferably 1.

Suitable examples of amidobetaines include cocoamidoethylbetaine, cocoamidopropylbetaine or lauramidobetaine or mixtures thereof. A preferred amidobetaine is cocoamidopropylbetaine which has been found to be especially compatible with CPC in mouthwash formulations.

Suitably the CPC is present in the range 0.005 to 10%, preferably 0.01 to 5%, more preferably 0.02 to 2.5% by weight of the mouthwash.

Suitably the amidobetaine is present together with another surfactant selected from a nonionic, another amphoteric or a cationic surfactant, or mixtures thereof.

Suitable nonionic surfactants include, for example, polyethoxylated sorbitol esters, in particular polyethoxylated sorbitol monoesters, for instance, PEG(40) sorbitan di-isostearate, and the products marketed under the trade name 'Tween' by ICI; polycondensates of ethylene oxide and propylene oxide (poloxamers), for instance the products marketed under the trade name 'Pluronic' by BASF-Wyandotte; condensates of propylene glycol; polyethoxylated hydrogenated castor oil, for instance, cremophors; and sorbitan fatty esters.

Suitable alternative amphoteric surfactants include, for example, long chain imidazoline derivatives such as the product marketed under the trade name 'Miranol C2M' by Miranol and long chain alkyl betaines, such as the product marketed under the tradename 'Empigen BB' by Albright+Wilson and mixtures thereof.

Suitable cationic surfactants include the D,L-2-pyrrolidone-5-carboxylic acid salt of ethyl-N-cocoyl-L-arginate, marketed under the trade name CAE by Ajinomoto Co. Inc., and cocamidopropyl PG dimonium chloride phosphate and lauramidopropyl PG dimonium chloride phosphate, available under the trade names Monaquat PTC and Monaquat PTL, respectively, from Mona Corporation.

Suitably between 50 to 100% of the surfactant is present as an amidobetaine.

Preferably between 65 to 90% of the surfactant is present as an amidobetaine.

More preferably an amidobetaine is present as the sole surfactant.

Suitably the total surfactant is present in the range 0.01 to 20%, preferably 0.05 to 10%, more preferably 0.1 to 5% by weight of the mouthwash.

Suitable mouthwash formulations will have an aqueous base comprising water or aqueous ethanol, and optionally a further liquid such as glycerin or propylene glycol. Mouthwash compositions may be provided in a "ready to use" form; as a concentrated solution, for dilution by the user immediately prior to use; or in solid form, such as a tablet or in a sachet, for dissolution by the user immediately prior to use. Tablets may suitably be prepared using xylitol and/or sorbitol as the major ingredient. The sachets and tablets may be formulated to provide, on dissolution, a still mouthwash, or, by the incorporation of a suitable effervescent couple, for instance sodium carbonate/bicarbonate and citric acid, an effervescent mouthwash.

Such compositions will contain appropriate formulating agents such as humectants, thickening agents, flavouring agents, sweetening agents, colouring agents and preservatives selected from those conventionally used in the oral hygiene composition art for such purposes and which are compatible with CPC and the surfactants hereinbefore described.

Suitable thickening agents include, for instance, nonionic thickening agents such as, for example, $(C_{1-6})$alkylcellulose ethers, for instance methylcellulose; hydroxy$(C_{1-6})$ alkylcellulose ethers, for instance hydroxyethylcellulose and hydroxypropylcellulose; $(C_{2-6})$alkylene oxide modified $(C_{1-6})$alkylcellulose ethers, for instance hydroxypropyl methylcellulose; and mixtures thereof. Other thickening agents such as natural and synthetic gums or gum like material such as Irish Moss, gum tragacanth, sodium carboxymethylcellulose, polyvinyl pyrrolidone, starch and thickening silicas may also be used.

Advantageously the thickening agent is present in the range 0.01 to 30%, preferably 0.1 to 15%, more preferably 1 to 5%, by weight of the composition.

Suitable humectants for use in compositions of the invention include for instance, glycerine, sorbitol, propylene glycol or polyethylene glycol, or mixtures thereof; which humectant may be present in the range from 5 to 70%, preferably 5 to 30%, more preferably 10 to 30% by weight of the composition.

Such compositions of the present invention may usefully further comprise an anti-caries agent, for instance a source of fluoride ions such as an alkali metal or amine fluoride salt, for example sodium fluoride, tin (II) fluoride. Alternatively, the fluoride ion source may be an alkali metal monofluorophosphate salt, for example sodium monofluorophosphate, optionally used in combination with an agent such as calcium glycerophosphate which is known to enhance the activity of monofluorophosphate (GB 1 384 375, Beecham Group). Suitably the composition will comprise between 50 and 2500 ppm, preferably 100 and 1500 ppm of fluoride ions, and most preferably 100–250 ppm.

Such compositions of the present invention may also comprise other active agents conventionally used in oral hygiene compositions, for instance: an alternative anti-plaque agent such as chlorhexidine or triclosan in addition to CPC; an anti-calculus agent such as a tetra- or a di-alkali metal pyrophosphate salt, or a mixture thereof, an alkali metal tripolyphosphate salt or an azacycloheptane diphosphonate salt; or an anti-sensitivity agent such as strontium acetate, strontium chloride or a potassium salt such as potassium nitrate, potassium chloride or potassium citrate. Such agents will be included at levels to provide the desired therapeutic effect and which are compatible with CPC.

Mouthwash compositions according to the present invention will have a pH which is orally acceptable, typically ranging from about pH 4 to 10, eg 5.5 to 8.

Mouthwash compositions according to the present invention may be prepared by admixing the ingredients in the appropriate relative amounts in any order that is convenient and thereafter and if necessary adjusting the pH to give the final desired value.

The invention also provides a method for combatting oral bacteria and the prophylaxis or treatment of mouth odour, periodontal disease, plaque, calculus and/or caries which method comprises the application of a composition according to the invention to the oral cavity.

The following examples illustrate the invention

EXAMPLE 1

(Use of Nonionic Surfactant)

A mouthwash was made up as follows:

|  | % W/W |
| --- | --- |
| Cremophor RH60* | 0.2 |
| CPC | 0.05 |
| Flavour | 0.12 |
| Ethanol | 15.00 |
| NaF | 0.05 |
| Saccharin | 0.052 |
| Patent Blue-V-0.5% | 0.075 |
| Chlorophyllin | 0.01 |
| De-Ionised Water | 84.443 |

*Cremophor RH60 is a polyethoxylated hydrogenated castor oil containing on average 60 ethoxy units in the polyethoxylated chain.

EXAMPLE 2

(Use of Nonionic Surfactant)

A mouthwash was made up as follows:

|  | % W/W |
| --- | --- |
| Cremophor RH60 | 0.2 |
| CPC | 0.05 |
| Flavour | 0.12 |
| Ethanol | 8.00 |
| NaF | 0.023 |
| Saccharin | 0.04 |
| NHDC (Neohesperidine DC) | 3.00 |
| Patent Blue-V-0.5% | 0.075 |
| Chlorophyllin | 0.01 |
| Deionised Water | 88.482 |

EXAMPLE 3

(Use of Cocamidopropylbetaine)

A mouthwash was made up as follows:

|  | % W/W |
| --- | --- |
| Cocoamidopropylbetaine | 0.2 |
| CPC | 0.05 |
| Flavour | 0.12 |
| Ethanol | 15.00 |
| NaF | 0.05 |
| Saccharin | 0.052 |
| Patent Blue-V-0.5% | 0.075 |
| Chlorophyllin | 0.01 |
| De-Ionised Water | 84.443 |

EXAMPLE 4

(Use of Cocamidopropylbetaine)

A mouthwash was made up as follows:

|  | % W/W |
| --- | --- |
| Cocoamidopropylbetaine | 0.2 |
| CPC | 0.05 |
| Flavour | 0.12 |
| Ethanol | 8.00 |
| NaF | 0.023 |
| Saccharin | 0.04 |
| NHDC (Neohesperidine DC) | 3.00 |
| Patent Blue-V-0.5% | 0.075 |
| Chlorophyllin | 0.01 |
| Deionised Water | 88.482 |

EXAMPLE 5

(Use of Cocoamidopropylbetaine)

A mouthwash was made up as follows:

|  | % W/W |
| --- | --- |
| Cocoamidopropylbetaine | 0.65 |
| CPC | 0.05 |
| Flavour | 0.13 |
| Ethanol | 15.00 |
| NaF | 0.05 |
| Saccharin | 0.06 |
| Patent Blue-V-0.5% | 0.075 |
| Chloropyllin | 0.01 |
| De-Ionised Water | 83.975 |

EXAMPLE 6
(Use of Cocoamidopropylbetaine and Nonionic Surfactant)
A mouthwash was made up as follows:

|  | % W/W |
| --- | --- |
| Cocoamidopropylbetaine | 0.10 |
| Cremophor RH60 | 0.05 |
| CPC | 0.05 |
| Flavour | 0.13 |
| Ethanol | 15.00 |
| NaF | 0.05 |
| Saccharin | 0.06 |
| Patent Blue-V-0.5% | 0.075 |
| Chloropyllin | 0.01 |
| Deionised water | 84.475 |

EXAMPLE 7
(Use of Cocoamidopropylbetaine)
A mouthwash was made up as follows:

|  | % W/W |
| --- | --- |
| Cocoamidopropylbetaine | 0.30 |
| CPC | 0.05 |
| Flavour | 0.13 |
| Ethanol | 15.00 |
| NaF | 0.05 |
| Saccharin | 0.06 |
| Patent Blue-V-0.5% | 0.075 |
| Chloropyllin | 0.01 |
| Deionised water | 84.475 |

EXAMPLE 8
(In-vitro Studies on Enamel/Hydroxyapetite Discs)

Hydroxyapatite discs or bovine enamel of known surface area are prepared by placing a 3 inch piece of cotton thread on the disc or in the empty root canal of the tooth. If HA discs are to be used the thread is stuck to the disc using nail varnish. If bovine enamel is to be used a thin film of a light body vinyl polysiloxane (eg Reprosil) is spread over the exposed dentine of the tooth, this serves to hold the cotton in place and to mask off the exposed dentine, preventing CPC binding to this area. The teeth or HA discs are then placed in sterile universals(1 tooth per universal) 5 mls of filtered pooled whole human saliva is then pipetted in to each sterilin. The teeth are then incubated overnight at 37° C. The following day each tooth is individually rinsed in deionised water (25 ml) for 15 seconds. This is then followed by a one minute treatment with the CPC mouthwash or simple solution (10 ml). The tooth is then rinsed 3 times in deionised water (25 ml), the Reprosil and cotton removed and the tooth is then immersed in 5 ml of a 50% acetonitrile, 30% tetrahydrofuran, 19.9% deionised water, 0.1% pentane sulphonic acid solution for 3 minutes to remove the CPC bound to the tooth/disc. The solution is then placed in an appropriate HPLC vial and analysed for its CPC content. This provides binding details. For retention details the same protocol is followed but before the tooth is immersed in the acetonitrile/THF/pentane sulphonic acid mixture it is immersed in 5 mls of filter pooled whole human saliva for 2 hours at 37° C. then the procedure is continued as for the binding experiment.

Upon examination of the binding of CPC to Hydroxyapatite discs from mouthwashes compared to simple solutions it was discovered that approx. 66% of the binding capacity of CPC was lost from the mouthwash:

Mouthwash of Example 1 1.68 $\mu$g/cm$^2$ CPC bound to disc
0.05% CPC SIMPLE SOLUTION IN WATER 5.36 $\mu$g/cm$^2$ CPC bound to disc (n=5)

This suggests that excipients in the mouthwash could be reducing the CPC binding. We therefore examined the mouthwash of Example 1 minus each excipient in turn to ascertain which might be having the most adverse effect on CPC binding.

Mouthwash of Example 1 1.62 $\mu$g/cm$^2$ CPC bound to disc
Mouthwash of Example 1 MINUS CREMOPHOR RH60 (solubiliser) 2.611 $\mu$g/cm$^2$ CPC bound to disc (n=5)

Also we looked at simple CPC solutions (0.05%) containing just one of the excipients in turn to again ascertain as to which were having adverse effects 0.05% CPC SIMPLE SOLUTION IN WATER 5.52 $\mu$g/cm$^2$ CPC bound to disc
0.05% CPC SIMPLE SOLUTION+CREMOPHOR RH60 2.36 $\mu$g/cm$^2$ CPC bound to disc (n=5)

The solubiliser, Cremophor RH60, was found to be the excipient having the major effect in reducing CPC binding.

Various solubilisers were examined as regards binding/retention of CPC to bovine enamel. Solubilisers examined were Tween 80, Tween 20, Pluronic F127, Pluronic F108, Cremophor RH40 and Cremophor RH60 at various levels in the mouthwash of Example 1 but none of these looked any more promising than with Cremophor RH60 at 0.2% (n=10)

Following on from this another solubiliser, Tegobetain (cocoamidopropylbetaine), was examined at various levels (0.2%, 0.4% and 1%) compared to Cremophor RH60 (0.2%) in the mouthwash formulation of Example 1:

Mouthwash of Example 3 1.44 $\mu$g/cm$^2$ CPC retained on bovine enamel.
Mouthwash of Example 1 0.60 $\mu$g/cm$^2$ CPC retained on bovine enamel.

An encouraging result was thus obtained using 0.2% of the cocoamidopropylbetaine surfactant which clearly improved the retention of CPC to bovine enamel.

A further study on modified formulations yielded the following results:

Mouthwash of Example 2 0.58 $\mu$g/cm$^2$ CPC retained on bovine enamel
Mouthwash of Example 4 0.93 $\mu$g/cm$^2$ CPC retained on bovine enamel
Mouthwash of Example 2 1.23 $\mu$g/cm$^2$ CPC bound to bovine enamel.
Mouthwash of Example 4 2.54 $\mu$g/cm$^2$ CPC bound to bovine enamel.

These results demonstrated that cocoamidopropylbetaine is significantly more compatible with CPC than nonionic surfactants and generally improves the binding and retention of CPC to bovine enamel.

Another study demonstrated that a higher level of cocoamidopropylbetaine was similarly advantageous:

Mouthwash of Example 5 0.95 $\mu$g/cm$^2$ CPC retained on bovine enamel
Mouthwash of Example 1 0.68 $\mu$g/cm$^2$ CPC retained on bovine enamel Two further studies on a mixed solubiliser system were conducted and the following results were obtained:

Mouthwash of Example 6 2.56 $\mu$g/cm$^2$ CPC bound to bovine enamel
Mouthwash of Example 1 1.62 $\mu$g/cm$^2$ CPC bound to bovine enamel
Mouthwash of Example 6 1.15 $\mu$g/cm$^2$ CPC retained on bovine enamel
Mouthwash of Example 1 0.68 $\mu$g/cm$^2$ CPC retained on bovine enamel The results obtained indicate that an amphoteric amidobetaine surfactant either alone or in admixture with another surfactant improves the binding and retention of CPC to bovine enamel when compared to mouthwash formulations containing solely a nonionic surfactant such as Cremophor RH60.

EXAMPLE 9
(In Vitro Studies on Mucosal Cells)

Human buccal epithelial cells were collected using a polypropylene spatula and dislodged into 20 mls of a Resting Saliva Salts (RSS) buffer (50 mM sodium chloride, 1.1 mM calcium chloride, 0.6 mM potassium dihydrogen orthophosphate) which were stored on ice. The cells were then washed three times by centrifugation in 20 ml RSS buffer and resuspended in RSS buffer at a final concentration of 1 ml per volunteer. Any remaining cell clumps were broken up by ultrasonic vibration. The cells were then counted using a haemocytometer.

Mouthwashes of example 1 and 6 and the cell suspension were warmed to 37° C. in an incubator. The cell suspension was then added (in 0.5 ml aliquots) to glass test-tubes. These were then centrifuged and the supernatant was discarded. 0.5 ml of the mouthwashes was then added to the cell pellets and these were vortexed briefly to suspend the cells in the mouthwash. They were then incubated and shaken gently at 37° C.

After five minutes the cells were harvested by centrifugation. The cells collected as the pellet were then washed three times in 2 ml RSS buffer. 1.5 ml of CPC mobile phase (50% acetonitrile, 30% tetrahydrofuran, 20% water with 0.1% pentanesulphonic acid) was added to each pellet and mixed vigorously by vortex and left for five minutes. These were then centrifuged and the supernatant was then analysed for CPC by HPLC. The following results were obtained:

Mouthwash of Example 1, 6.07 µg CPC bound/100000 cells

Mouthwash of Example 6, 9.57 µg CPC bound/100000 cells

These results demonstrate that the amidobetaine surfactant in combination with another surfactant allows for a significant increase in CPC bound to mucosal cells compared to a similar product without amidobetaine.

EXAMPLE 10
(Microbiological Retention Results)

Hydroxyapatite discs were pellicle coated by soaking in saliva. These discs were soaked in test solutions for two minutes followed by two washes in deionised water. Test solutions were tested neat and in a 1 in 5 dilution. The discs were then placed onto surfaces of an agar plate seeded with *Propionobacter acnes*. The agar was Brain Heart Infusion agar and the plate was incubated at 37° C. for 2 days anaerobically.

Zones of inhibition were measured to ascertain the microbiological activity of retained CPC on the discs.

Mouthwash of Example 1 gave zones of inhibition of 18.65 for 1:5 dilution and 21.08 neat.

Mouthwash of example 6 gave zones of inhibition of 20.11 for 1:5 dilution and 23.58 neat.

A placebo mouthwash, containing no CPC but with cocoamidopropylbetaine showed no activity neat or in a 1:5 dilution and a 0.05% CPC solution gave zones of inhibition of 20.98 for 1:5 dilution and 24.83 neat.

The results obtained indicate that the amidobetaine surfactant in combinations with another surfactant provides for increased CPC retention on hydroxyapatite discs and demonstrates the microbiological activity of this retained CPC.

These results complement those from the binding and retention studies on enamel and HA discs in Example 8.

EXAMPLE 11
(Microbiological Activity)

Mechanisms that are sensitive to changes in membrane potential provide a means of assessing the viability of the cell. In bacteria, the cellular apparatus for energy metabolism is localised on the cytoplasmic inner membrane. This potential decreases and death follows when the membrane is perturbed by physical or chemical agents. Fluorescent probes have been examined as indicators of bacterial viability using Flow Cytometry. Of these bis-(1,3-dibutylbarbituric acid) trimethine oxonol (DiBAC4(3)) is the most sensitive and robust. It is also applicable to high throughput flow cytometry assays. The negatively charged oxonol dye undergoes potential dependent distributions between the cytoplasm and the extracellular membrane and enters depolarised (i.e. dead) cells where it binds to lipid rich components. The fluoresence is enhanced upon accumulation.

CPC is a cationic quaternary ammonium compound and acts on the cell membrane and results in a generalised loss of function. Such a loss would be reflected as an increase in the uptake of oxonol (DiBAC4(3)) and consequent increase in fluoresence indicating cell death. As CPC is the primary active in the mouthwashes of the application it was decided to test their relative efficacy against Streptococcus mutans using oxonol (DiBAC4(3)) and a Biorad Bryte Flow Cytometer. This was carried out as follows:

100 µl of each of Mouthwash of example 7, Mouthwash of example 1 and CPC+amidobetaine control were added to 2 ml volumes of PBS with approximately 107 Streptococcus mutans NCTC 10904 per ml. To each of these three solutions was added 10 µl of a 1 mg/ml solution of oxonol. Change in fluoresence was monitored over 20 minutes using the Biorad Bryte Flow Cytometer. For each of the three test solutions, the mean fluoresence channel number (excitation 470–495/emission 520–550 nm) was plotted against time. The plot shown in FIG. 1 clearly shows greater fluoresence by S.mutans in the presence of Mouthwash of example 7 as compared with the Mouthwash of example 1. This indicates that significantly greater cell damage (at p<0.05) has been done to the S.mutans organism by the amido betaine containing formulation than by the formulation without.

These results further confirm the advantage for amidobetaine with CPC.

What is claimed is:

1. A mouthwash composition consisting essentially of between about 0.005 to about 10% by weight of CPC; an orally acceptable carrier or excipient and between about 0.01 to about 20% by weight of an amidobetaine of the formula:

$$RC(O)NH(CH_2)_a N^+(R^1)(R^2)(CH_2)_b CO_2^-$$

wherein

R is $C_{10-20}$ alkyl;

$R^1$ and $R^2$ are independently $C_{1-4}$ alkyl;

a is an integer from 1 to 4; and b is an integer from 1 to 4.

2. A composition according to claim 1 wherein the amidobetaine is selected from cocoamidoethylbetaine, cocoamidopropylbetaine or lauramidobetaine or mixtures thereof.

3. A composition according to claim 2 wherein the amidobetaine is cocoamidopropylbetaine.

4. A composition according to claim 1 wherein the amidobetaine is present together with another surfactant selected from a nonionic, another amphoteric or a cationic surfactant, or mixtures thereof.

5. A composition according to claim 4 wherein between 50 to 100% of the surfactant is present as an amidobetaine.

6. A composition according to claim 4 wherein between 65 to 90% of the surfactant is present as an amidobetaine.

7. A composition according to claim 1 wherein an amidobetaine is present as the sole surfactant.

* * * * *